(12) United States Patent
Zhou et al.

(10) Patent No.: US 8,703,971 B2
(45) Date of Patent: Apr. 22, 2014

(54) THIOPHENE-CONTAINING ORGANIC PHOTOELECTRIC MATERIALS, THEIR PREPARATION METHODS AND SOLAR CELL DEVICES

(75) Inventors: Mingjie Zhou, Shenzhen (CN); Jie Huang, Shenzhen (CN); Hui Liu, Shenzhen (CN)

(73) Assignee: Ocean's King Lighting Science & Technology Co., Ltd., Shenzhen, Guangdong (CN)

( * ) Notice: Subject to any disclaimer, the term of this patent is extended or adjusted under 35 U.S.C. 154(b) by 0 days.

(21) Appl. No.: 13/514,947

(22) PCT Filed: Dec. 14, 2009

(86) PCT No.: PCT/CN2009/075548
§ 371 (c)(1),
(2), (4) Date: Jun. 8, 2012

(87) PCT Pub. No.: WO2011/072435
PCT Pub. Date: Jun. 23, 2011

(65) Prior Publication Data
US 2012/0241004 A1    Sep. 27, 2012

(51) Int. Cl.
*C07D 409/14*    (2006.01)
*C07D 409/04*    (2006.01)
*H01L 31/042*    (2006.01)

(52) U.S. Cl.
USPC .......................................... 549/59; 136/263

(58) Field of Classification Search
None
See application file for complete search history.

(56) References Cited

FOREIGN PATENT DOCUMENTS

CN    101208349 A    6/2008
CN    101282959 A    10/2008

OTHER PUBLICATIONS

Gallazzi, Maria C. et al.; Polythiophenes with Unusual Electrical and Optical Properties Based on Donor Acceptor Alternace Strategy; 2001; Macromolecular Chemistry and Physics, 202 No. 10; pp. 2074-2084.*
Gallazi et al. (Macromol. Chem. Phys. 2001, 202, 2074-2085).*
Gallazzi Maria C. et al: "Polythiophenes with unusual electrical and optical properties based on donor acceptor alternance strategy", Macromol Chem. Phys., vol. 202, No. 10, 2001, pp. 2074-2085, XP008157164.
Schulze, Kerstin et al: "Efficient heterojunction organic solar cells with high photovoltage containing a low gap oligothiophene derivative", Proc. of SPIE, vol. 6192, 2006, pp. 61920C/1-61920C/6, XP008157173.
Schueppel R. et al: "Optimizing organic photovoltaics using tailored heterojunctions: a photoinduced absorption study of oligothiophenes with low band gaps", Physical Review B, vol. 77, No. 8, 2008, pp. 085311 1-085311 14, XP008157174.

* cited by examiner

*Primary Examiner* — Noble Jarrell
*Assistant Examiner* — Valerie Rodriguez-Garcia
(74) *Attorney, Agent, or Firm* — Shimokaji & Associates P.C.

(57) ABSTRACT

Provided are thiophene-containing organic photoelectric materials represented by structural formula (1). The materials are thiophene compounds having multiple thiophene rings and cyano groups, useful in solar cell applications. One primary compound, for example, derivative of dicyanoethenyl quinquethiophene is well suited for application as electron donor material. Preparation methods of these thiophene-containing organic photoelectric materials and solar cell devices containing the above thiophene-containing organic photoelectric materials also are provided. Due to the fact that thiophene rings and cyano groups are included, the above thiophene-containing organic photoelectric materials have broader spectra respondence, better thermal stability and environmental stability.

3 Claims, 3 Drawing Sheets

THIOPHENE-CONTAINING ORGANIC PHOTOELECTRIC MATERIALS, THEIR PREPARATION METHODS AND SOLAR CELL DEVICES

FIELD OF THE INVENTION

The present invention relates to the technical field of organic materials, and more particularly to the thiophene-containing organic photoelectric materials, their preparation methods and solar cell devices.

BACKGROUND OF THE INVENTION

Today, the world economy is mainly built on the basis of fossil energy, such as coal, oil and natural gas. However, the non-renewable fossil energy is constantly depleting. Since the beginning of the 21st century, global energy issues and the consequent issues about environmental pollution and global warming become more apparent and gradually intensified. Solar energy has the outstanding advantages such as widespread and broad distribution, large amount, pollution-free, clean, safe and convenient obtained, so it is considered to be one of the most promising renewable energy. Solar cells transfer the solar energy into electricity directly, which is an effective and feasible method of using solar energy. However, the current commercial solar cells are restricted to silicon and other inorganic solar cells, while their prices are so expensive that exceed general acceptable degree currently, which greatly limit their use. In order to reduce the cost and expand the scope of application, for a long time, people have been looking for the new solar cell materials.

Organic solar cells is a new type of solar cells, compared with the inorganic semiconductor materials of the limited source, expensive price, toxicity, complex preparation process and high cost, it has some advantages that inorganic solar cells can not match, such as wide sources of materials, diversity and regulation of the structure, low cost, safety and environmental protection, simple preparation process, light weight, and can be flexiblly prepared in large areas, etc., which can be widely used in the field of architecture, lighting and power generation, with important development and application prospects. Therefore, many domestic and international research institutions and enterprises are all given considerable attention and investment to it. So far, however, the photoelectric conversion efficiency of the organic solar cells is much lower than the inorganic solar cells's. Therefore, it has great significance for improving the efficiency of the organic solar cells and other semiconductor devices that the development of new organic photoelectric materials.

SUMMARY OF THE INVENTION

For this reason, the present invention provides the thiophene-containing organic photoelectric materials which have broader spectra respondence and better stability, and the preparation methods of these thiophene-containing organic photoelectric materials which have the simple synthetic route and low cost.

The present invention also provides the solar cell devices containing the above thiophene-containing organic photoelectric materials.

Thiophene-containing organic photoelectric materials, which comprise the compounds represented by structural formula (1):

(1)

wherein, $R_1$, $R_2$, $R_3$ and $R_4$ are the same or different and represent hydrogen or straight, branched or cyclic alkyl containing 1 to 12 carbon atoms, m, n and p are the same or different integer between 0 and 6.

Preparation methods of the thiophene-containing organic photoelectric materials, which comprise the following steps:

chemical compounds A, B and C represented by the following structural formulas and malononitrile are provided respectively,

A:

B:

C:

wherein, $R_1$, $R_2$, $R_3$ and $R_4$ are the same or different and represent hydrogen or straight, branched or cyclic alkyl containing 1 to 12 carbon atoms, m, n and p are the same or different integer between 0 and 6;

under the conditions of the catalyst/solvent, the compounds A and B react with malononitrile respectively as the condensation reaction, or the compounds A and B react with C as the Stille coupling reaction;

under the conditions of the catalyst/solvent, the condensation reaction products react with C as the Stille coupling reaction, or the Stille coupling reaction products react with malononitrile as the condensation reaction, and the compounds represented by the following structural formula (1) are obtained:

(1)

As well as, the solar cell devices, which comprise glass substrate, transparent anode, middle additional layer, active layer and the cathode, and they are successively stacked, the active layer comprises electron donor materials and electron acceptor materials, and the electron donor materials are the above thiophene-containing organic photoelectric materials.

In the above thiophene-containing organic photoelectric materials, the thiophene has the structure of five-rings, according to Hückel's rule, thus have moderate bandgap, broader spectra respondence, better thermal stability and environmental stability. Moreover, the above thiophene-containing organic photoelectric materials have two pairs of cyano, and cyano groups are the electron withdrawing groups, thus can further widening the spectra respondence range of materials, and can also improve the optical and electrical properties of the materials. In the above preparation methods of the thiophene-containing organic photoelectric materials, the synthetic route is simple, thereby reduces the preparation costs. Through using the thiophene-containing organic photoelectric materials, which can not only improve the photoelectric conversion efficiency and can reduce the quality of solar cell devices, and facilitate the preparation of large quantities.

BRIEF DESCRIPTION OF THE DRAWINGS

Further description of the present invention will be illustrated, which combined with embodiments in the drawings.

DETAILED DESCRIPTION OF ILLUSTRATED EMBODIMENTS

In order to make the purpose, the technical solutions and the benefits of the present invention more clearly understand, the following embodiments which combine with the drawings are provided to descript the present invention further details. It should be understood that the specific embodiments described herein is only used to explain the present invention, not used to limit the present invention.

Figure 1:
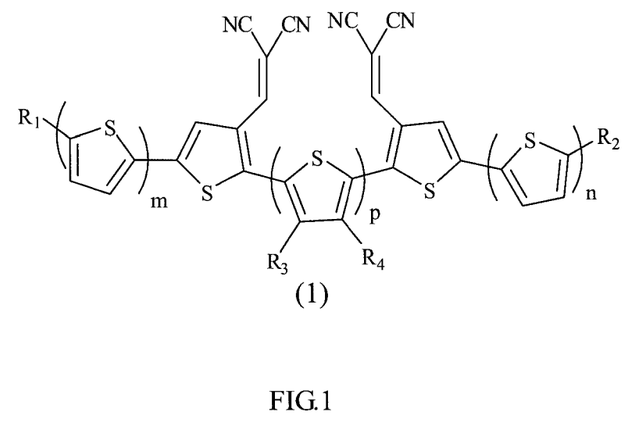
FIG. 1 shows the schematic diagram of the structural formula (1) of the thiophene-containing organic photoelectric materials, which is prepared in the embodiment of present invention.

See FIG. 1, FIG. 1 shows the structural formula (1) of the thiophene-containing organic photoelectric materials prepared in the embodiment of present invention, which comprise the following structural formula (1):

(1)

wherein, $R_1$, $R_2$, $R_3$ and $R_4$ are the same or different and represent hydrogen or straight, branched or cyclic alkyl containing 1 to 12 carbon atoms, m, n and p are the same or different integer between 0 and 6.

In one embodiment of the present invention, the thiophene-containing organic photoelectric materials have symmetrical molecular structure, for example m=n. In another embodiment of the present invention, m=n=p=0, when the thiophene-containing organic photoelectric materials have the structure of dual thiophene, the lower molecular weight and the lighter quality products. In a preferred embodiment of the present invention, $R_1$ and $R_2$ are the same groups, such as the straight chain alkyl containing 6 carbon atoms, and that is, they are hexyl, while preferred, $R_3$ and $R_4$ are hydrogen. In another preferred embodiment of the present invention, preferred, m, n and p are 1, that is, the thiophene-containing organic photoelectric materials are the derivatives of quinquethiophene.

Figure 2:
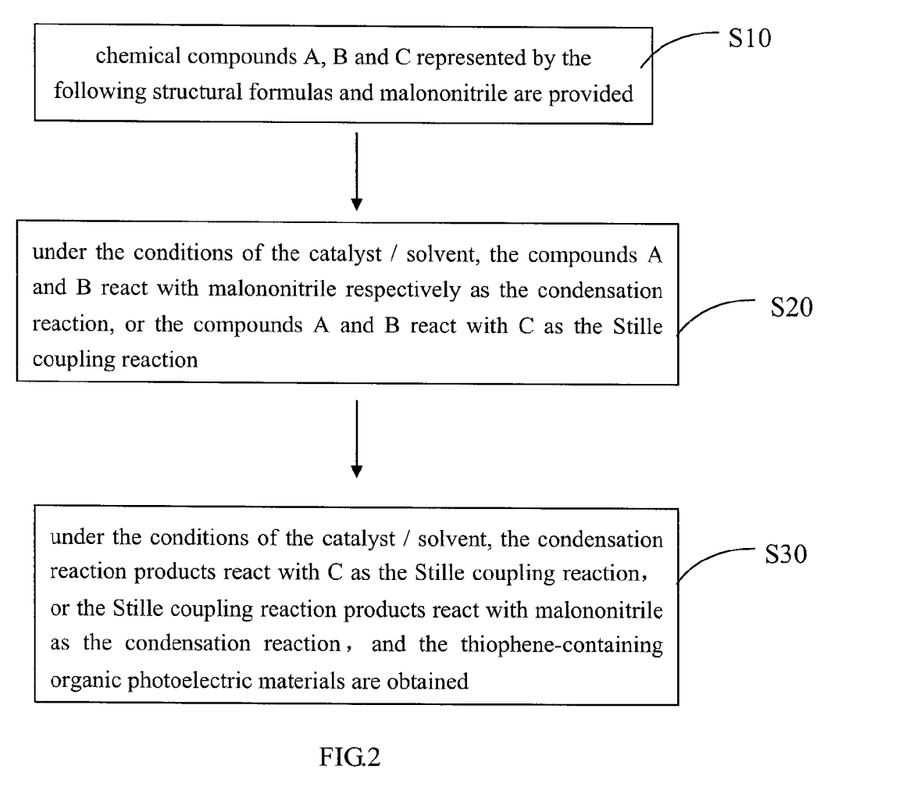
FIG. 2 shows the flow chart of the preparation methods of the thiophene-containing organic photoelectric materials, which is prepared in the embodiment of present invention.

See FIG. 2, FIG. 2 shows the preparation methods of the above thiophene-containing organic photoelectric materials, which comprise the following steps:

S10: chemical compounds A, B and C represented by the following structural formulas and malononitrile are provided respectively, wherein, $R_1$, $R_2$, $R_3$ and $R_4$ are the same or different and represent hydrogen or straight, branched or cyclic alkyl containing 1 to 12 carbon atoms, m, n and p are the same or different integer between 0 and 6;

S20: under the conditions of the catalyst/solvent, the compounds A and B react with malononitrile respectively as the condensation reaction, or the compounds A and B react with C as the Stille coupling reaction;

S30: under the conditions of the catalyst/solvent, the condensation reaction products react with C as the Stille coupling reaction, or the Stille coupling reaction products react with malononitrile as the condensation reaction, and the compounds represented by the following structural formula (1) are obtained:

In step S10, the compounds A, B, C and malononitrile can be purchased from the market directly or can be prepared through the synthetic methods in the prior art, which are not detailed herein. Therein, the descriptions are the same with the above thiophene-containing organic photoelectric materials. In one embodiment of the present invention, the thiophene-containing organic photoelectric materials have symmetrical molecular structure, such as m=n, thus the corresponding raw materials of compounds A and B are the same. In another embodiment of the present invention, m=n=p=0, when the thiophene-containing organic photoelectric materials have the structure of dual thiophene, the lower molecular weight and the lighter quality products, and the source of corresponding raw materials is extensive. In a preferred embodiment of the present invention, $R_1$ and $R_2$ are the same groups, such as the straight chain alkyl containing 6 carbon atoms, and that is, they are hexyl, while preferred, $R_3$ and $R_4$ are hydrogen. In another preferred embodiment of the present invention, preferred, m, n and p are 1.

In steps S20 and S30, according to the condensation reaction and the Stille coupling reaction have the different order, the present invention can be achieved by two schemes. The first scheme is: under the conditions of the catalyst/solvent, the compounds A and B react with malononitrile respectively as the condensation reaction, thus the aldehyde groups in compounds A and B are substituted by 2-methylenemalononitrile respectively. Then, under the conditions of the catalyst/solvent, the condensation reaction products react with C as the Stille coupling reaction and the thiophene-containing organic photoelectric materials are obtained. The second scheme is: under the conditions of the catalyst/solvent, the compounds A and B react with C as the Stille coupling reaction, and the derivatives of quinquethiophene with two aldehyde groups are obtained, then the derivatives of quinquethiophene react with malononitrile as the condensation reaction, and the two aldehyde groups in derivatives of quinquethiophene are substituted by 2-methylenemalononitrile respectively, then the thiophene-containing organic photoelectric materials are obtained. The molar ratio of each reactant is 1:1 or other proportions, the following reactions can be carried out without affecting the reaction in this embodiment. They are introduced in the following respectively.

The first scheme comprises the following steps:

Step i: under the conditions of the catalyst/solvent, the compounds A and B react with malononitrile respectively as the condensation reaction, and the aldehyde groups in compounds A and B are substituted by 2-methylenemalononitrile, and the compounds A' and B' are obtained respectively, the reaction process is shown as follows:

Specifically, in step i the catalyst is pyridine or triethylamine, preferred, it is pyridine; solvent is ethanol, methanol, dichloromethane, chloroform, tetrahydrofuran (THF), ethyl acetate, DMF, toluene or acetone, preferred, it is ethanol. In addition, when the reaction is complete, to purify further, in particular: washing the reaction products with saturated sodium chloride solution several times, extracting and drying, after filtering, collecting the filtrate for the rotary evaporation, and then getting the purified products through using silica gel column chromatography. Therein, the extractant can be ethyl acetate, the desiccant can be anhydrous magnesium sulfate, and the silica gel column chromatography can be carried out with petroleum ether: ethyl acetate as eluent.

Step ii: under the conditions of the catalyst/solvent, the compounds A' and B' obtaining in step i react with C as the Stille coupling reaction, and the thiophene-containing organic photoelectric materials are obtained, the reaction process is shown as follows:

Specifically, in step ii the catalyst can be the organic palladium catalyst, such as Pd$_2$(dba)$_3$/P(o-Tol)$_3$, Pd(PPh$_3$)$_4$ or Pd(PPh$_3$)$_2$Cl$_2$, preferred, it be Pd$_2$(dba)$_3$/P(o-Tol)$_3$. The solvent can be tetrahydrofuran (THF), dichloromethane, ethylene glycol dimethyl ether, benzene or toluene, preferred, it be THF. In addition, when the reaction is complete, to purify further, in particular: when the reaction products back to the room temperature, adding the KF solution, stirring a few minutes, then adding saturated sodium chloride solution, extracting and drying, filtering, then collecting the filtrate for rotary evaporation, and then taking precipitation twice with n-hexyl methane and ethanol, and using silica gel column chromatography to purify the crude products obtained by filtering, finally getting the purified products. Therein, the extractant can be ethyl acetate, the desiccant can be anhydrous magnesium sulfate, and silica gel column chromatography can be carried out with petroleum ether: dichloromethane as eluent. When the compounds A' and B' react with compound C as the Stille coupling reaction, if m≠n, in theory, compounds A' and B' itself will react with compound C as the Stille coupling reaction, and form the compounds with (2m+p+2) and (2n+p+2) thiophene rings respectively, while the yield of the purpose products in the above reaction is low, the purified products as structural formula can be obtained by the above purification steps. It could be understood that, at this point, the compounds with (2m+p+2) and (2n+p+2) thiophene rings also can be purified and to be as the thiophene-containing organic photoelectric materials, which belongs to the scope of the present invention to protect. When m=n, compounds A and B' are the same, the product yield is high, approximately is more than 80%.

The second scheme comprises the following steps:

Step i': the compounds A and B react with C as the Stille coupling reaction, and the derivatives of quinquethiophene with two aldehyde groups are obtained, the reaction process is shown as follows:

Specifically, in the second scheme, the reaction conditions of step i' are basically the same with the step ii of the first scheme', and the product yield are the same, which are not discussed herein.

Step ii: the derivatives of quinquethiophene with two aldehyde groups obtaining in step i' react with malononitrile as the condensation reaction, and the two aldehyde groups in derivatives of quinquethiophene are substituted by 2-methylenemalononitrile respectively, then the above thiophene-containing organic photoelectric materials are obtained, the reaction process is shown as follows:

Specifically, in the second scheme, the reaction conditions of step ii' are basically the same with the step i of the first scheme', which are not discussed herein.

The above thiophene-containing organic photoelectric materials comprise more than one thiophene ring, have the modest bandgap and the broader spectra respondence, the band is around 250-650 nm which covering the visible light band, also have the better thermal stability and environmental stability, and showing the better optical and electrical properties. Therefore, the thiophene-containing organic photoelectric materials are the materials which can be used widely, for example, they can be used in the fields of organic solar cells, organic field-effect transistors, organic electroluminescence, organic optical storage, organic nonlinear materials and organic laser.

Figure 3:
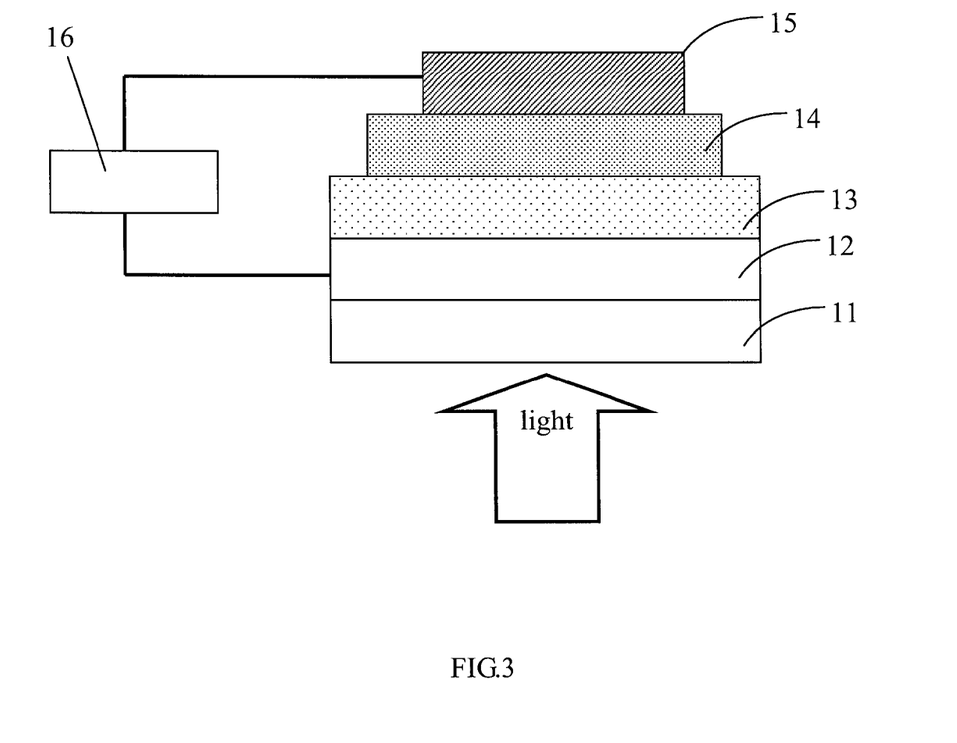
FIG. 3 shows the schematic diagram of the structure of the solar cell devices containing thiophene-containing organic photoelectric materials, which is prepared in the embodiment of present invention.

See FIG. 3, FIG. 3 shows the solar cell devices containing the thiophene-containing organic photoelectric materials prepared in the above embodiments, which comprise glass substrate 11, transparent anode 12, middle additional layer 13, active layer 14 and the cathode 15, and they are successively stacked, the middle additional layer 13 could be used by the composite materials of poly(3,4-ethylene-dioxy-thiophene)-polystyrene sulphonic acid (referred to as PEDOT: PSS), the active layer 14 comprises electron donor materials and electron acceptor materials, and the electron donor materials could be used by the above thiophene-containing organic photoelectric materials, the electron acceptor materials can be [6,6]-phenyl-$C_{61}$-methyl butyrate (referred to as PCBM), the transparent anode 12 could be used by the indium tin oxide (referred to as ITO), preferred, it is a sheet indium tin oxide with resistance of 10-20Ω/. The cathode 15 can be the aluminum electrode. Therein, glass substrate 11 can be the bottom, when preparing, at first, the ITO electrode be deposited on the glass substrate 11, then the middle auxiliary layer 13 form on the ITO electrode, and the thiophene-containing organic photoelectric materials and the electron acceptor materials be deposited on the middle auxiliary layer 13 by vacuum evaporation, and to form the active layer 14, and then depositing the cathode 15 be deposited on the active layer 14 by vacuum evaporation technology, the above solar cell devices are obtained.

As shown, under light radiation, the light penetrate the glass substrate 11 and the ITO electrode 12, the thiophene-containing organic photoelectric materials in the active layer 14 absorb solar energy and form exciton, then the exciton move to the interface of the electron donor/acceptor materials and transfer electrons to the electron acceptor materials such as PCBM, thus achieve the charge separation, and then form the free charge carriers, that is, free electrons and holes. These free electrons pass to the metal cathode along the electron acceptor materials and be collected by the cathode, while the free holes pass to the ITO anode along the electron donor materials and be collected by the anode, thus form the photocurrent and photovoltage to complete photoelectric conversion, which is connected to the external load 16, can be supplied power. In this process, the thiophene-containing organic photoelectric materials have wide spectra respondence range, thus can be able to make better use of solar energy, and to obtain the higher photoelectric conversion efficiency, increase the capacity of the electricity production of solar cell devices. And this organic material can reduce the quality of solar cell devices, and can be produced through technologies such as vacuum evaporation, thus facilitate the preparation of large quantities.

The thiophene-containing organic photoelectric materials of preparation methods and properties are illustrated in the following embodiments.

Embodiment 1

Embodiment 1 the thiophene-containing organic photoelectric materials such as 2,2'-((5,5''''-dihexyl-[2,2':5',2'':5'',2''':5''',2''''-quinquethiophene]-3''',4'-diyebis(methanylylidene))dimalononitrile, the structural formula is shown as follows:

It is known by the structural formula, the thiophene-containing organic photoelectric materials in embodiment 1 have the symmetrical structure, five-thiophene rings and two pairs of cyano, and the cyano is the electron withdrawing group, because of the symmetrical structure, the thiophene-containing organic photoelectric materials have the better properties of light adsorption and photoelectricity, compared with the other more than one thiophene ring-containing materials. The preparation methods of the five-thiophene by taking the first scheme, the specific operations are shown as follows:

1) Prepare the 2-((5-bromo-5'-hexyl-[2,2'-bithiophen]-4-yl)methylene)malononitrile, the structural formula is shown as follows:

Due to the thiophene-containing organic photoelectric materials in embodiment 1 have the symmetrical structure, so, in this step, the structure of compounds A and B are the same, and the products are the same, that is, the structure of compounds A' and B' are the same, thus the step 1) is needed only once, which simplify the craft and reduce the cost. If the thiophene-containing organic photoelectric materials don't have the symmetrical structure, the structure of compounds A and B are not the same, then the step 1) is needed for different raw materials. The specific operations are: adding 50.0 mL ethanol, 0.90 g (2.52 mmol) 5-bromo-5'-hexyl-[2,2'-bithiophene]-4-carbaldehyde (belongs to A or B) and 0.19 g (2.80 mmol) malononitrile in order, heating to reflux. Then adding three drops pyridine quickly, reacting over night. Washing the reaction products with saturated sodium chloride solution several times, extracting by ethyl acetate and drying by anhydrous magnesium sulfate, after filtering, collecting the filtrate for the rotary evaporation, then getting golden yellow solider products through using silica gel column chromatography which with petroleum ether:ethyl acetate (20:1) as eluent, the product yield is 83%. GC-MS m/z=405.

2) prepare the 2,2'-(5,5''''-dihexyl-[2,2':5',2'':5'',2''':5''',2''''-quinquethiophene]-3''',4'-diyl)bis(methanylylidene))dimalononitrile, the structural formula is shown as follows:

The specific operations are: adding 50 mL THF into the pressure pipe, adding 0.61 g (1.50 mmol) 2-((5-bromo-5'-hexyl-[2,2'-bithiophen]-4-yl)methylene)malononitrile (belongs to A' or B') and 0.46 g (0.70 mmol) 2,5-bis(tributylstannyl)thiophene belongs to C) quickly, then admitting nitrogen to the bellow of the surface of solution for 10 min, then adding 0.013 g (0.014 mol) $Pd_2(dba)_3$ and 0.0083 g (0.027 mmol) $P(o\text{-Tol})_3$, and admitting nitrogen to the bellow of the surface of solution to exclude oxygen for 10 min, then covering, warming up to 80° C., reacting over night. when the reaction is complete, the reaction products back to the room temperature, adding 10.0 mL (1.00 M) KF solution, stirring 30 minutes, adding saturated sodium chloride solution, extracting by ethyl acetate and drying by anhydrous magnesium sulfate, filtering, and collecting the filtrate for rotary evaporation, and then taking precipitation twice with n-hexyl methane and ethanol respectively, and using silica gel column chromatography which with petroleum ether:dichloromethane (1:2) as eluent, to purify the crude products obtained by filtering, finally getting the dark purple powder products, the product yield is 81%. GC-MS m/z=733.

Embodiment 2

To take the same end products five-thiophene with embodiment 1 for example, the specific operations of preparation method of the five-thiophene according to the first scheme are shown as follows:

1) prepare the 5,5''-dihexyl-[2,2':5',2'':5'',2''':5''',2''''-quinquethiophene]-3''',4'-dicarbaldehyde the structural formula is shown as follows:

Due to the thiophene-containing organic photoelectric materials in embodiment 2 have the symmetrical structure, so, in this step, the structure of compounds A and B are the same, thus the step 1) is needed only once, which simplify the craft and reduce the cost.

The specific operations are: adding 15 mL THF into the pressure pipe, adding 0.36 g (1.00 mmol) 5-bromo-5'-hexyl-[2,2'-bithiophene]-4-carbaldehyde and 0.33 g (0.50 mmol) 2,5-bis(tributylstannyl)thiophene quickly, then admitting nitrogen to the bellow of the surface of solution for 10 min, then adding 0.0092 g (0.010 mol) $Pd_2(dba)_3$ and 0.0061 g (0.020 mmol) $P(o\text{-Tol})_3$, and admitting nitrogen to the bellow of the surface of solution to exclude oxygen for 10 min, then covering, warming up to 80° C., reacting over night. when the reaction is complete, the reaction products back to the room temperature, adding 10.0 mL (1.00M) KF solution, stirring 30 minutes, then adding saturated sodium chloride solution, extracting by ethyl acetate and drying by anhydrous magnesium sulfate, after filtering, collecting the filtrate for the rotary evaporation, then getting purple powder products through using silica gel column chromatography which with petroleum ether:dichloromethane (3:1) as eluent, the product yield is 71%. GC-MS m/z=637.

2) prepare the 2,2'-((5,5''''-dihexyl-[2,2':5',2'':5'',2''':5''',2''''-quinquethiophene]-3''',4'-diyl)bis(methanylylidene))dimalononitrile, which is the same with embodiment 1.

The specific operations are: adding 40.0 mL ethanol, 0.20 g (0.32 mmol) 5,5''''-dihexyl-[2,2':5',2'':5'',2''':5''',2''''-quinquethiophene]-3''',4'-dicarbaldehyde and 0.046 g (0.70 mmol) malononitrile in order, heating to reflux. Then adding three drops pyridine quickly, reacting over night. Washing the reaction products with saturated sodium chloride solution several times, extracting by ethyl acetate and drying by anhydrous magnesium sulfate, after filtering, collecting the filtrate for the rotary evaporation, then taking precipitation twice with n-hexyl methane and ethanol respectively, and using silica gel column chromatography which with petroleum ether: dichloromethane (1:2) as eluent to purify the crude products obtained by filtering, finally getting the dark purple powder products, the product yield is 53%. GC-MS m/z=733.

From the foregoing, in the above thiophene-containing organic photoelectric materials, the thiophene has the structure of five-rings, according to Hückel's rule, thus have moderate bandgap, broader spectra respondence, better thermal stability and environmental stability. Moreover, the above thiophene-containing organic photoelectric materials have two pairs of cyano, and cyano groups are the electron withdrawing groups, thus can further widening the spectra respondence range of materials, and can also improve the optical and electrical properties of the materials. In the above preparation methods of the thiophene-containing organic photoelectric materials, the synthetic route is simple, thereby reduces the preparation costs. Through using the thiophene-containing organic photoelectric materials, which can not only improve the photoelectric conversion efficiency and can reduce the quality of solar cell devices, and facilitate the preparation of large quantities.

The above embodiments are the preferred embodiments of the present invention, which are not used to limit the present invention, thus any changes, equivalent replacement and improvement made within the spirit and principles of the present invention, should be included in the scope of the present invention to protect.

What is claimed is:
1. Thiophene-containing organic photoelectric materials, which represented by structural formula (1):

(1)

wherein, $R_3$ and $R_4$ are the same or different and represent hydrogen or straight, branched or cyclic alkyl containing 1 to 12 carbon atoms, m, n and p are the same or different integer between 1 and 6, $R_1$ and $R_2$ are the same and represent straight chain alkyl containing 6 carbon atoms.

2. The thiophene-containing organic photoelectric materials according to claim 1, wherein, the $R_3$ and $R_4$ represent hydrogen both.

3. The thiophene-containing organic photoelectric materials according to claim 1, wherein, the m, n and p all are 1.

* * * * *